United States Patent [19]
Cabrera et al.

[11] Patent Number: 5,849,473
[45] Date of Patent: Dec. 15, 1998

[54] METHOD OF LYOPHILIZATION OF MAMMALIAN SPERM CELLS

[75] Inventors: Gonzalo M. Cabrera, Carson; Raymond P. Goodrich, Jr., Pasadena, both of Calif.

[73] Assignee: COBE Laboratories, Inc., Lakewood, Colo.

[21] Appl. No.: 656,194

[22] Filed: Feb. 15, 1991

[51] Int. Cl.⁶ .............................. A01N 1/02; A61K 35/52
[52] U.S. Cl. .................................................. 435/2; 424/561
[58] Field of Search .................................. 435/2; 424/561

[56] References Cited

U.S. PATENT DOCUMENTS 4,874,690  10/1989  Goodrich et al. ............................ 435/2

OTHER PUBLICATIONS

Grant and Hacth's Chemical Dictionary p.364 (1987).
Singh et al Indian J. Vet. Sci 37: 1–7 (1967).
Watanabe et al J. Fac. Fish. Anim. Husb. 11:33–37 (1972).

*Primary Examiner*—Sandra E. Saucier
*Attorney, Agent, or Firm*—Finnegan, Henderson, Farabow, Garrett & Dunner, L.L.P.

[57] ABSTRACT

A method is provided for the lyophilization of mammalian sperm cells which can be stored and reconstituted to provide morphologically intact cells. The method is advantageous in that the sperm cells may be stored at ambient temperatures for extended periods of time and recovered morphologically intact with DNA-containing heads and intact flagella. The lyophilization medium comprises a carbohydrate and a polymer selected from PVP, HES, dextran and poloxamers or mixtures thereof.

14 Claims, No Drawings

METHOD OF LYOPHILIZATION OF MAMMALIAN SPERM CELLS

FIELD OF THE INVENTION

This invention relates to the general field of biochemistry and medical sciences, and specifically to a method of lyophilizing and reconstituting mammalian sperm cells.

BACKGROUND OF THE INVENTION

The presently used method of long term storage of mammalian sperm cells, required for human sperm banks and for livestock breeding, is by maintenance at liquid nitrogen temperatures. The length of time that the cells can be stored under these conditions is therefore cost-limited since at some point during the storage period the cost of consumption of liquid nitrogen makes further storage economically unfeasible. There is a need, therefore, for a method for storing sperm cells for prolonged periods of time in a cost efficient manner, while still maintaining the cells morphologically intact to be useful for in vitro or in vivo fertilization.

It is therefore an object of the present invention to provide a method for lyophilizing mammalian sperm cells which permits prolonged storage times at ambient temperatures and which still allows for reconstitution of the cells in a morphologically intact form.

SUMMARY OF THE INVENTION

The present invention provides a method for lyophilizing mammalian sperm cells by mixing the sperm cells with a buffered solution comprising a carbohydrate and a polymer or mixture of polymers having a number average molecular weight in the range of about 1K to 600K, then drying the cells by sublimation of water. If desired, the sperm cells may be diluted with an extender prior to lyophilization. The lyophilized cells may be maintained for prolonged periods under ambient temperatures and then restored using reconstitution buffers containing polymers, phosphate buffered saline containing glucose and adenine and/or other cell metabolites such as ATP or NAD.

DETAILED DESCRIPTION OF THE INVENTION

The sperm cells treated according to the present invention may be used in a neat form or diluted with an extender such as egg yolk. Preferably if an extender is used, the concentration of the sperm cells in the extender will be in the range of about 10% to 50% by volume. The preferred sperm cells are those for commercial livestock fertilization such as porcine or bovine sperm cells, however the present invention may also be applicable for the preservation of human sperm cells.

The lyophilization buffer according to the present invention will contain a carbohydrate, typically in the concentration of about 0.1 to 2.6 molar. Preferably the carbohydrate may be selected from the group consisting of monosaccharides and disaccharides but monosaccharides are preferred, particularly glucose. Other monosaccharides such as xylose, ribose, mannose and fructose may also be employed.

The lyophilization buffer will also contain a polymer or a mixture of polymers having a number average molecular weight in the range of about 1K to 600K, preferably in the range of about 1K to 350K. These polymers are preferably amphipathic. While not intending to be bound by any theory, the amphipathic properties of the polymers are believed to allow them to bind to the cell membrane while protecting the membrane's surface by extension of the hydrophilic portion into the aqueous environment. This may alleviate the damage to the cell membrane. The preferred polymers are selected from the group consisting of polyvinylpyrrolidone (PVP) and polyvinylpyrrolidone derivatives, dextran and dextran derivatives, hydroxyethyl starch and poloxamers. Most preferred is a polyvinylpyrrolidone of an average molecular weight in the range of about 10K to 40K, preferably about 30K in a concentration range of about 10% to 30% weight/volume in the lyophilization buffer prior to lyophilization. Amino acid based polymers (proteins), dextrans or hydroxyethyl starch are also useful as are other amphipathic polymers such as poloxamers in any of their various forms.

The term lyophilization is broadly defined as freezing a substance and then reducing the concentration of one of the solvents, namely water, by sublimation and desorption, to levels which will no longer support biological or chemical reactions. This is usually accomplished by a drying step in a high vacuum.

The lyophilization buffer will be buffered in the range of about pH 7.0 to 7.4, preferably by a phosphate-buffered saline solution. A typical phosphate-buffered saline solution will comprise mono- and di-basic sodium phosphate, sodium chloride and potassium chloride, in amounts which typically maintain the pH at around 7.2.

Upon lyophilization by conventional techniques, the lyophilized sperm cells may be maintained under vacuum in vacuum type containers or under nitrogen or other inert gas at room temperatures for extended periods of time in the absence of or without significant degradation of their desirable morphological properties when reconstituted for use. It is a particular advantage of the present invention that the lyophilized sperm cells may be stored at room temperature for extended periods of time.

It is a further advantage of the present invention that the lyophilized sperm cells may be reconstituted at normal temperatures, i.e., greater than about 17° C. up to about 37° C., and preferably at about room temperature, 22° C. A preferred reconstitution medium is a solution comprising a polymer or mixture of polymers as described above, preferably having a number average molecular weight in the range of about 1K to 30K, preferably about 15K and phosphate-buffered saline containing glucose and adenine (PBSGA). The reconstitution solution will also preferably contain typical cell metabolites such as ATP and NAD. The polymer used may be the same polymer utilized to lyophilize the sperm cells as described above. Hence the polymers polyvinylpyrrolidone, hydroxyethyl starch, dextran or other amphipathic polymers are particularly preferred with the most preferred being polyvinylpyrrolidone. The reconstitution solution will be typically buffered by phosphate-buffered saline solution containing adenine and glucose to maintain the pH in the range of about 7.0 to 7.4. The most particularly preferred polymer is polyvinylpyrrolidone of an average number molecular weight of about 15K.

The reconstitution buffer may also optionally contain a monosaccharide such as xylose, glucose, ribose, mannose, and fructose (in addition to the glucose in the PBSGA solution). A typical monosaccharide concentration would be about 1 molar in the reconstitution buffer. A 1 molar fructose concentration is particularly useful. In the most preferred embodiment, lyophilized sperm cells are reconstituted by mixing with an equal volume of reconstitution buffer at ambient temperature and mixed until fully hydrated. By equal it is meant that the volume is the same as the starting volume prior to lyophilization. After reconstitution, the cells may be used for in vitro fertilization.

The lyophilized sperm cells are advantageously restorable at ambient atmospheric temperatures (usually about 20° to 30° C.) and can be reconstituted to morphologically intact states having intact DNA in the heads and intact tails. By intact tails it is noted that by and large the flagella of the cells are intact. These cells may be used for in vitro fertilization and it is contemplated that upon mixing with appropriate cofactors, motility may be induced for potential in vivo use as well.

Having described the preferred embodiments of the present invention, the following examples are provided by way of illustration but are not intended to limit the invention in any way.

EXAMPLE

Various samples of boar and bull sperm were collected and used either in neat form or diluted 1:1 with an extender (egg yolk). A basic lyophilization buffer was prepared containing 3.1 mM potassium chloride, 1.5 mM potassium hydrogen phosphate, 91.9 mM sodium chloride, 4.3 mM disodium hydrogen phosphate, 2.6M of glucose and 26% w/v Plasdone C-30 (PVP,MW30K). This was called lyophilization Buffer A. A second lyophilization buffer was prepared containing the same components except that 16% Plasdone C-30 was used in 1.6M glucose. This was called lyophilization Buffer B. A third lyophilization buffer was used containing 16% Plasdone C-30, 1.6M glucose containing egg yolk extender. This was called lyophilization Buffer C.

Six preparations containing boar sperm were prepared containing, respectively, 50% neat sperm, 10% neat sperm and 10% neat sperm in Buffers A, B and C, and 50% of 1:1 ratio sperm in extender, 10% of 1:1 mixture and 10% of 1:1 mixture in Buffers A, B and C. Five preparations containing bull sperm were prepared containing, respectively, 10% neat sperm in Buffer B and 10% neat sperm in Buffer C, 50% 1:1 sperm and extender in Buffer A, 10% 1:1 sperm and extender in Buffer B and 10% 1:1 sperm and extender in Buffer C. All eleven samples were lyophilized and reconstituted in four different buffers as follows:

Buffer 1: 19% Plasdone C-15.

Buffer 2: 19% Plasdone C-15/5 mM ATP/0.47 mM NAD.

Buffer 3: PBSGA.

Buffer 4: PBSGA/5 mM ATP/0.47 mM NAD.

After reconstitution the morphology and motility of the sperm cells were observed under a microscope. In all cases morphologically the cells were intact with no broken flagella. The sperm cells were non-motile but would apparently be useful for in vitro fertilization. The cells were then incubated in PBSGA with 1M fructose at 37° C. (or alternatively at room temperature) for 30 minutes. The sperm morphology was not altered, but no motility was observed.

From the foregoing description, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and although specific terms have been employed herein, they are intended in a descriptive sense and not for purposes of limitation.

What is claimed is:

1. A method for lyophilizing mammalian sperm cells comprising the steps of mixing a composition containing said sperm cells with a buffered solution comprising; a carbohydrate and a polymer or mixture of polymers selected from the group consisting of polyvinylpyrrolidone, hydroxyethyl starch, dextran and poloxamers, said polymers having a number average molecular weight in the range of about 1K to 600K; and drying said cells by sublimation of water.

2. A method according to claim 1 wherein said composition comprises egg yolk.

3. A method according to claim 1 wherein the sperm cell concentration in said composition is in a range of 10% to 50% by volume.

4. A method according to claim 1 wherein said sperm cells are selected from the group consisting of porcine, bovine and human sperm cells.

5. A method according to claim 1 wherein said average molecular weight is in the range of 1K to 350K.

6. A method according to claim 1 wherein the concentration of said polymers in said solution is in the concentration range from 0.5 to 30% weight/volume.

7. A method according to claim 1 wherein said carbohydrate comprises a monosaccharide.

8. A method according to claim 7 wherein said monosaccharide comprises glucose.

9. A method according to claim 1 wherein the concentration of said carbohydrate and said solution is in a range of 0.1 to 2.6 molar.

10. A method for preparing reconstituted sperm cells comprising the step of lyophilizing said sperm cells with a buffered solution comprising a carbohydrate and a polymer or mixture of polymers selected from the group consisting of polyvinylpyrrolidone, hydroxyethyl starch, dextran and poloxamers having a number average molecular weight in the range of about 1K to 600K; reconstituting the lyophilized composition containing said sperm cells with a sufficient volume of reconstitution buffer to rehydrate said sperm cells in a morphologically intact form with intact DNA containing heads and intact tails.

11. A method according to claim 10 wherein said polymers have a molecular weight in the range of about 1K to 30K.

12. A method according to claim 11 wherein said polymers have an average molecular weight of about 15K.

13. A method according to claim 10 wherein said reconstitution buffer comprises phosphate-buffered saline with glucose and adenine.

14. A method according to claim 13 wherein said reconstitution buffer further comprises cell metabolites.

* * * * *